(12) United States Patent
Insel et al.

(10) Patent No.: US 10,107,816 B2
(45) Date of Patent: Oct. 23, 2018

(54) G-PROTEIN COUPLED RECEPTOR-ASSOCIATED DIAGNOSTICS AND THERAPEUTICS FOR B-CELL CHRONIC LYMPHOCYTIC LEUKEMIA

(71) Applicant: THE REGENTS OF THE UNIVERSITY OF CALIFORNIA, Oakland, CA (US)

(72) Inventors: Paul Insel, San Diego, CA (US); Fiona Murray, San Diego, CA (US); Lingzhi Zhang, San Diego, CA (US); Trishna Katakia, Downey, CA (US); Andrea Wilderman, San Diego, CA (US); Charles Gray, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 139 days.

(21) Appl. No.: 14/782,804

(22) PCT Filed: Apr. 8, 2014

(86) PCT No.: PCT/US2014/033284
§ 371 (c)(1),
(2) Date: Oct. 7, 2015

(87) PCT Pub. No.: WO2014/168922
PCT Pub. Date: Oct. 16, 2014

(65) Prior Publication Data
US 2016/0349261 A1 Dec. 1, 2016

Related U.S. Application Data

(60) Provisional application No. 61/809,678, filed on Apr. 8, 2013.

(51) Int. Cl.
*G01N 33/574* (2006.01)
*A61K 38/22* (2006.01)

(52) U.S. Cl.
CPC ....... *G01N 33/57426* (2013.01); *A61K 38/22* (2013.01); *G01N 2333/726* (2013.01); *G01N 2800/7028* (2013.01)

(58) Field of Classification Search
CPC ....... G01N 33/57426; G01N 2333/726; G01N 2800/7028; A61K 38/22
See application file for complete search history.

(56) References Cited

U.S. PATENT DOCUMENTS

| 2009/0004193 A1 | 1/2009 | Golz et al. |
| 2011/0052502 A1 | 3/2011 | Croce et al. |

OTHER PUBLICATIONS

International Search Report in related PCT Application No. PCT/US2014/033284, dated Nov. 5, 2014.
Bomben et al., "Comprehensive characterization of IGHV3-21—expressing B-cell Chronic Lymphocytic Leukemia: an Italian multicenter study," Blood, 2007, vol. 109(7), p. 2989-98.
Katakia et al., "Disease stage-specific G protein-coupled receptor expression in clinical disorders: Chronic lymphocytic leukemia as a model," The FASEB Journal, 2012, vol. 26.
Katakia, Trishna Chetan, "G protein-coupled receptor expression and function in malignant B-cells : Therapeutic targets for Chronic Lymphocytic Leukemia," Master Thesis University of California, San Diego, 2012.
TagMan Life Technologies, "Custom TagMan Array Cards," product bulletin, Jan. 31, 2012.
Wong et al., "Real-time PCR for mRNA quantitation," Biotechniques, vol. 39, No. 1, Jul. 2005, pp. 75-85.
Insel et al., "Cyclic AMP is both a pro-apoptotic and antiapoptotic second messenger," Acta Physiolog (Oxford) 2012; 204: 277-87.
Insel et al., "GPCR expression in tissues and cells: are the optimal receptors being used as drug targets?" Brit. Journal of Pharmacology 2012; 165: 1613-6.
Peiro et al., "Genetic variation in phosphodiesterase (PDE) 7B in chronic lymphocytic leukemia: overview of genetic variants of cyclic nucleotide PDEs in human disease," J Hum Genet. Sep. 2011; 56(9):676-81.
Malavasi et al., "CD38 and chronic lymphocytic leukemia. a decade later," Blood. 2011; 118: 3470-8.
Zent et al., "Management of patients with chronic lymphocytic leukemia with a high risk of adverse outcome: the Mayo Clinic approach," Leuk Lymphoma 2011; 52: 1425-34.
Zhang et al., "Cyclic nucleotide phosphodiesterase 7B mRNA: an unfavorable characteristic in chronic lymphocytic leukemia," Int J Cancer. Sep. 1, 2011; 129(5):1162-9.
Ben-Ami et al., "Gq protein-induced apoptosis is mediated by AKT kinase inhibition that leads to protein kinase C-induced c-Jun N-terminal kinase activation" J Biol Chem. 2011; 286: 31022-31.
Macor et al. "An update on the xenograft and mouse models suitable for investigating new therapeutic compounds the treatment of B-cell malignancies," Curr Pharm Des. 2008; 14:2023-39.
Zhang et al., "Cyclic nucleotide phosphodiesterase profiling reveals increased expression of phosphodiesterase 7B in chronic lymphocytic leukemia," Proc Nat Acad Sci USA. 2008; 105: 19532-7.
Yanamadala et al., "Ga12 stimulates apoptosis in epithelial cells through JNK1 mediated BCL-2 degradation and up-regulation of TKBa," JBiol Chem. 2007; 282: 24352-63.
Burger et al., "CXCR4: a key receptor in the crosstalk between tumor cells and their microenvironment," Blood. 2006; 107: 1761-7.
Burger et al., "Blood-derived nurse-like cells protect chronic lymphocytic leukemia B cells from spontaneous apoptosis through stromal cell derived factor-1," Blood. 2000; 96:2655-63.

*Primary Examiner* — Ruixiang Li
(74) *Attorney, Agent, or Firm* — Eversheds Sutherland (US) LLP

(57) ABSTRACT

The disclosure provides diagnostic and therapeutic agents for chronic lymphocytic leukemia (CLL). Further provided are biomarkers and a biomarker panel comprising G-protein coupled receptors (GPCRs) specifically expressed by CLL cells. Methods for diagnosing a disease stage of a CLL patient, progression, or prediction of clinical course and drug selection for the CLL patient, as well as methods for treating CLL, by targeting these GPCR biomarkers are also provided.

2 Claims, 8 Drawing Sheets

G-PROTEIN COUPLED RECEPTOR-ASSOCIATED DIAGNOSTICS AND THERAPEUTICS FOR B-CELL CHRONIC LYMPHOCYTIC LEUKEMIA

CROSS-REFERENCE TO RELATED APPLICATIONS

This application is a US National Stage of International Application No. PCT/US2014/033284, filed 8 Apr. 2014, which claims the benefit of U.S. Provisional Application No. 61/809,678, filed 8 Apr. 2013, the entire content of which is fully incorporated by reference herein.

FIELD OF THE INVENTION

The invention relates generally to diagnostics and therapeutics for leukemia, particularly chronic lymphocytic leukemia (CLL).

BACKGROUND OF THE INVENTION

Various publications, including patents, published applications, technical articles and scholarly articles are cited throughout the specification. Each of these cited publications is incorporated by reference herein, in its entirety.

G protein-coupled receptors (GPCR) are guanine nucleotide exchange factors for heterotrimeric G-proteins, whose α and βγ subunits dissociate and regulate effectors. $G\alpha_s$ stimulates adenylyl cyclase, and $G\alpha_i$ inhibits adenylyl cyclase. GPCRs are the largest receptor family (~3% of genome) and are the largest class of attractive drug targets in disease since they are expressed on the plasma membrane and are tissue specific.

CLL is the most common form of adult leukemia in the Western world. It is characterized by the accumulation of CD5+, CD19+ and CD23+ B-cells due to decreased apoptosis. CLL shows a highly variable clinical course spanning from indolent, slow growing to aggressive, which requires immediate treatment. A clinical problem for many heterogeneous diseases, such as chronic lymphocytic leukemia, is the lack of identification of molecular and cellular markers that can predict progression. Current agents for treating CLL include classical cancer chemotherapeutic drugs (such as alkylating agents that inhibit DNA synthesis), corticosteroids, agents toxic to cells, or certain antibodies that block other types of surface antigens. However, CLL is still considered as an incurable disease for which new diagnostic tools and new therapies are needed. Since CLL patients have two types: indolent (slowly progressive) and aggressive (rapidly progressive) disease, better ways are needed to diagnose, predict and treat those patients who progress from indolent to aggressive disease.

SUMMARY OF THE INVENTION

The invention provides a novel biomarker panel of diagnostic and therapeutic targets for CLL. More specifically, the invention provides that GPCRs, which are previously untested entities expressed in CLL cells, provide novel biomarker panels to diagnose, predict (as biomarkers) and serve as therapeutic targets for CLL. In certain embodiments, the invention provides that expression of GPCRs is unique or altered in either or both indolent and/or aggressive CLL cells showing different expression levels of GPCRs in different disease stages. In certain embodiments, the invention provides that normal B-cells expressed 200 GPCRs, 84 of which were orphan receptors. In contrast, indolent CLL (slow growing CLL form not requiring treatment) expressed 170 GPCR's, 72 of which were orphans, and aggressive CLL (CLL form requiring immediate treatment) expressed 117 GPCR's, 51 of which were orphan. FIGS. 1-4 provide venn diagrams showing numbers of GPCRs that are unique to either and/or both indolent CLL and/or aggressive CLL as compared to normal B-cells. Tables 1-8 further provide detailed lists of the GPCRs that are unique to either and/or both CLLs. One or more of isolated GPCRs listed in Tables 1-8, alone or in combination, constitute novel diagnostic biomarker panels and therapeutic targets for CLL.

In certain embodiments, the invention provides that the vasoactive intestinal polypeptide receptor 1 (VIPR1), a Gas-coupled GPCR, increased expression significantly (e.g. about 700-fold) in aggressive CLL and indolent CLL as compared to normal B-cells. The invention also provides that VIP increases apoptosis in aggressive CLL cells, but does not promote apoptosis in normal B-cells. The increased cAMP and apoptosis effect of VIP is significantly enhanced with a cyclic AMP phosphodiesterase 4/7 inhibitor, IR284. In certain embodiment, the invention provides that treatment with IR284 or VIP suppressed CLL cell proliferation.

In certain embodiments, the invention provides that the melanocortin 2 receptor (MC2R), also a Gas-coupled receptor, was also expressed significantly different in aggressive and indolent CLL-cells, as compared to normal B-cells, and levels of mRNA expression in CLL subtypes reflect cAMP product in response to ACTH, another phosphodiesterase inhibitor.

In other embodiments, the invention further provides that CLL cells express more mRNA and protein of leucine-rich repeat G protein-coupled receptor 8 (LGR8, aka GPR106, or Relaxin receptor 2), and the LGR8 agonist INSL3 protects CLL cells from spontaneous apoptosis.

Therefore, the pattern of expression of GRCRs, particularly VIPR1, MC2R, LGR8, as well as those listed in Tables 1-8, is useful as new blood and/or stage specific biomarkers for CLL, and/or therapeutic targets for preventing, treating or ameliorating CLL. Therefore, the invention provides disease stage-specific GPCRs, including but not limited to VIPR1, MC2R, LGR8, as well as those listed in Tables 1-8 in CLL, and a use of these disease stage-specific GPCRs as biomarkers for diagnosing stages of CLL, and/or as therapeutic targets for treating CLL. Biomarkers that are also therapeutic targets are attractive for personalize medicine.

The invention thus provides an identification of G-protein-coupled receptors (GPCRs) expressed by chronic lymphocytic leukemia (CLL) cells, and in turn, define effects of agonists and antagonists of particular GPCRs on cell growth and cell death and formation of second messengers by CLL cells. The GPCRs include receptors whose physiological agonists (activators) are known and other GPCRs (termed "orphan GPCRs") for which these agonists are not known. These orphan GPCRs are novel surface markers that have diagnostic utility and can be therapeutic targets for patients with CLL. Tables 1-8 provide detailed lists of the GPCRs that are unique to either and/or both CLLs. Ligands/drugs for each GPCR listed can be found in the GPCR database maintained by the International Union of Basic and Clinical Pharmacology and the British Pharmacological Society, the *IUPHAR/BPS* Guide to Pharmacology.

The invention further provides a method for inducing apoptosis in CLL cells and/or inhibiting CLL cell proliferation comprising administering to a subject in need a composition comprising an effective amount of an agent that targets one or more GPCR uniquely expressed in CLL cells.

In certain embodiments, the agent is a GPCR agonist or antagonist that interacts with said GPCRs uniquely expressed in CLL cells, altering an mRNA, DNA, or protein expression level of said GPCRs, or their associated secondary message signaling pathways. Agonist or antagonist of a GPCR can be a small molecule, as well as antibodies or other biologics, naturally occurring or synthetically made.

In certain embodiments, the composition comprises a GPCR agonist VIP that interacts with VIPR1 and its associated cAMP signaling pathway, resulting in increased apoptosis in CLL cells. In other embodiments, the composition further comprises a cyclic AMP phosphodiesterase 4/7 inhibitor selected from the group consisting of IR284, as an example of phosphodiesterase 4 and/or phosphodiesterase 7 inhibitors and ACTH. Treatment with specific GCPR agonists is useful in treating CLL. For example, apoptosis was induced in aggressive CLL cells, but not indolent CLL or normal B-cells, when treated with VIP, with or without a phosphodiesterase inhibitor (which results in cAMP accumulation), or treatment with ACTH, a selective MC2R agonist and a phosphodiesterase inhibitor. An increase in cAMP was also observed, which is associated with an increase in apoptosis. In yet other embodiments, the GPCR agent is peptide hormone insulin-like peptide 3 (INSL3) that interacts with LGR8 so as to protect CLL cells from spontaneous apoptosis. Antagonists of INSL3 or other agents that block LGR8 would thus be predicted to enhance the killing of CLL cells.

Therefore, the invention provides a composition, and method of use thereof, for diagnosing and/or treating CLL or its disease stage, comprising an agent, including agonist, antagonist, small molecule, biologic, or antibody, that targets one or more specific GPCRs expressed by the CLL cells, and a pharmaceutically acceptable carrier or excipient, with or without a second agent that modulate GPCR-related second message signaling pathway, such as the cAMP signaling pathway.

DETAILED DESCRIPTION OF THE INVENTION

Figure 1:
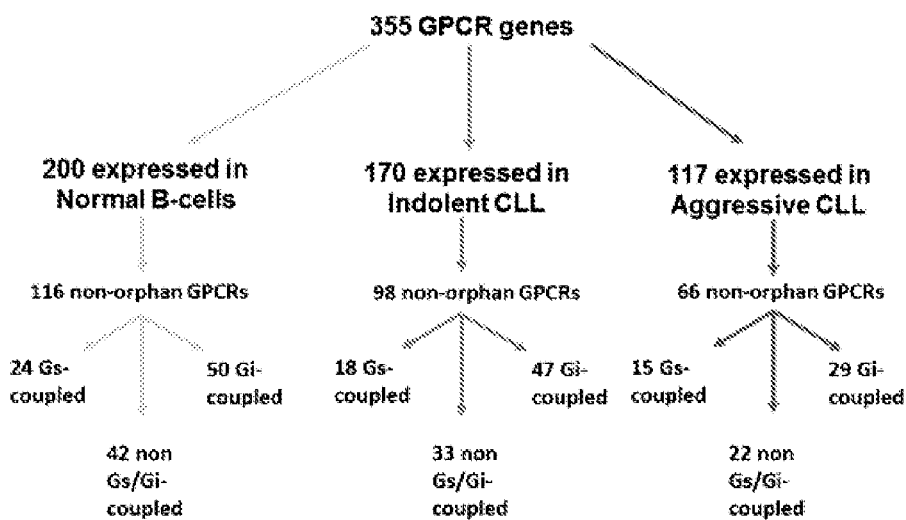
FIG. 1 represents a diagram indicating numbers of GPCR genes that are expressed in normal B-cells, indolent CLL, and aggressive CLL.

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific peptides or proteins, specific cell types, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. It is also to be understood that as used in the specification and in the claims, "a" or "an" can mean one or more, depending upon the context in which it is used. Thus, for example, reference to "a cell" can mean that at least one cell can be utilized.

The invention provides novel diagnostic (biomarkers) and therapeutic targets for CLL. In certain embodiments, the invention provides normal B-cells, indolent CLL, and aggressive CLL displayed varying patterns of GPCR expression. Numerous GPCRs are uniquely expressed in CLL compared to normal B-cells and between the two stages of CLL. In certain embodiments, the invention provides the GPCR array data revealing that certain GPCRs, such as VIPR1, MC2R, LGR8, and those listed in Tables 1-8 show significant difference in expression between aggressive and/or indolent CLL, as compared to normal B-cells. In certain embodiments, real-time PCT validation data confirm the increase in VIPR1 mRNA, as well as MC2R and LGR8 mRNAs and proteins in aggressive CLL and/or indolent CLL, as compared to those in normal B-cells. Therefore, these GPCRs expressed in indolent and/or aggressive CLL can serve as both biomarkers and targets for CLL diagnosis and treatment.

As used herein, the term "significantly and/or substantially difference" means statistically different, wherein the difference is subject to any statistical analysis with a P value of less than 0.05, preferably less than 0.01, more preferably less than 0.001.

As used herein, the term "expression level" refers to an amount of a gene and/or protein that is expressed in a cell. As used herein, a "gene" includes a polynucleotide containing at least one open reading frame that is capable of encoding a particular polypeptide or protein after being transcribed and translated. Any of the polynucleotide sequences described herein may also be used to identify larger fragments or full-length coding sequences of the gene with which they are associated. Methods of isolating larger fragment sequences are known to those of skill in the art.

As used herein, the terms "polynucleotide," "nucleic acid/nucleotide" and "oligonucleotide" are used interchangeably, and include polymeric forms of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, DNA, cDNA, genomic DNA, recombinant polynucleotides, branched polynucleotides, plasmids, vectors, isolated DNA of any sequence, isolated RNA of any sequence, nucleic acid probes, and primers. Polynucleotides may be naturally-occurring, synthetic, recombinant or any combination thereof.

As used herein, a "naturally-occurring" polynucleotide molecule includes, for example, an RNA (mRNA) or DNA molecule having a nucleotide sequence that occurs in nature (e.g., encodes a natural protein). As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant" also encompasses the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form. The "polynucleotide sequence" is the alphabetical representation of a polynucleotide molecule. A polynucleotide is composed of a specific sequence of four nucleotide bases: adenine (A); cytosine (C); guanine (G); thymine (T); and uracil (U) in place of guanine when the polynucleotide is RNA. This alphabetical representation can be inputted into databases in a computer and used for bioinformatics applications such as, for example, functional genomics and homology searching.

As used herein, the term "protein" or "polypeptide" is interchangeable, and includes a compound of two or more subunit amino acids, amino acid analogs, or peptidomimetics. The subunits may be linked by peptide bonds. In another embodiment, the subunit may be linked by other bonds, e.g., ester, ether, etc. As used herein, the term "amino acid" includes either natural and/or unnatural or synthetic amino acids, including both the D or L optical isomers, and amino acid analogs and peptidomimetics. A peptide of three or more amino acids is commonly referred to as an oligopeptide. Peptide chains of greater than three or more amino acids are referred to as a polypeptide or a protein.

The present invention provides that both mRNA and protein expression levels of certain GPCRs listed in Tables 1-8 in either or both indolent or aggressive CLL patients are significantly increased compared to those in normal subjects. In certain embodiments, the mRNA and/or protein expression levels in CLL patients are at least 2-fold higher as compared to that in normal subjects. Preferably, the mRNA expression level is 2-, 5-, 10-, 20-, 30-, 40-, 50-, 60-, 70-, 80-, 100-, 200-, 300-, 400-, 500-, 600-, 700-fold higher than that in normal subjects. In yet another preferred embodiment, the protein expression level in CLL patients is about 5-90-fold increased as compared to that in normal subjects. In yet other embodiments, both mRNA and protein expression levels in CLL patients are significantly decreased at least 2-fold as compared to those in normal subjects.

The present invention further provides a kit for a diagnosis of indolent and/or aggressive CLL comprising biomarker detecting reagents for determining expression levels of GPCRs, such as VIPR1, MC2R, LGR8, or any other GPCRs listed in Tables 1-8, and instructions for their use in diagnosing CLL. As used herein, the term "biomarker"

refers to an indicator and/or prognostic factor of biologic or pathologic processes or pharmacologic responses to a therapeutic intervention. As used herein, the term "prognostic factor" refers to any molecules and/or substances contributing to a predicted and/or expected course of CLL including various developments, changes and outcomes of the disease. As used herein, the term "detecting reagents" refer to any substances, chemicals, solutions used in chemical reactions and processes that are capable of detecting, measuring, and examining GPCRs. In other preferred embodiments, the biomarker detecting reagents used herein comprise chemicals, substances, and solutions that are suitable for determining either mRNA or protein, or both expression levels of GPCRs. One or more types of biomarker detecting reagents can be provided in solution or adhered to a microarray for detection.

One of the detecting reagents or therapeutic agents may include immunologically active molecules comprising an antibody molecule or a fragment thereof that specifically binds to a particular interested GPCR or an antigen for such GPCR. The term "antibody" as used herein encompasses monoclonal antibodies (including full length monoclonal antibodies), polyclonal antibodies, multispecific antibodies (e.g., bispecific antibodies), and antibody fragments so long as they exhibit the desired biological activity of binding to the interested GPCR. The term "antibody fragments" comprise a portion of a full length antibody, generally the antigen binding or variable region thereof. Examples of antibody fragments include Fab, Fab', $F(ab')_2$, and Fv fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The "monoclonal antibodies" may also be isolated from phage antibody libraries using the techniques known in the art.

The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

The term "single-chain Fv" or "sFv" antibody fragments comprise the VH and VL domains of antibody, wherein these domains are present in a single polypeptide chain. Generally, the Fv polypeptide further comprises a polypeptide linker between the VH and VL domains which enables the sFv to form the desired structure for antigen binding.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-polyacrylamide gel electrophoresis under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

In order to avoid potential immunogenicity of the monoclonal antibodies in human, the monoclonal antibodies that have the desired function are preferably humanized. "Humanized" forms of non-human (e.g., murine) antibodies are chimeric antibodies that contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. Antibodies capable of immunoreacting to particular GPCRs are made using conventional methods known in the art.

Other molecules which selectively bind to one or more GPCRs or their gene products (e.g. mRNAs) known to those skilled in the art, or discovered in the future, are contemplated within the scope of the present invention. Such molecules include primers and/or probes comprising desired DNA, RNA, and/or DNA/RNA hybrid sequences. As used herein, the term "primer" refers to a segment of DNA or RNA that is complementary to a given DNA or RNA sequences (e.g. sequences of a particular GPCR) and that is needed to initiate replication by DNA polymerase, and a term "probe" refers to a substance, such as DNA, that is radioactively labeled or otherwise marked and used to detect or identify another substance in a sample. As used herein, the term "primer" and "probe" are used interchangeably, and typically comprise a substantially isolated oligonucleotide typically comprising a region of nucleotide sequence that hybridizes under stringent conditions to at least about 12, preferably about 25, more preferably about 40, 50, or 75 consecutive nucleotides of a sense and/or an antisense strands of a nucleotide sequence of a particular interested GPCR; or naturally occurring mutants thereof. As used herein, primers based on the nucleotide sequence of a particular interested GPCR can be used in PCR reactions to clone homologs of these GPCRs. Probes based on the nucleotide sequences of these GPCRs and their isoforms can be used to detect transcripts or genomic sequences encoding the same or substantially identical polypeptides or proteins.

In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express or over-express these GPCRs, such as by measuring a level of encoding nucleic acid, in a sample of cells, e.g., detecting mRNA levels or determining whether a genomic gene has been mutated or deleted.

In certain preferred embodiments, the biomarkers and/or prognostic factors for diagnosing and monitoring CLL comprise the interested GPCRs, including but not limited to VIPR1, MC2R, LGR8, and one or more GPCRs listed in Tables 1-8. In yet certain preferred embodiments, the kit of the present invention comprise any detecting reagents that are capable to detect mRNA, protein, or both, expression levels of these GPCRs. The kit of the present invention further comprises an instruction for use in diagnosing and monitoring CLL. In one preferred embodiment, the instruction in the kit provides that an elevated mRNA and/or protein expression levels, or a decreased mRNA and/or protein expression levels of one or more interested GPCRs indicates an association with CLL, as well as the disease stage of CLL.

Furthermore, the present invention provides a method for inducing apoptosis and/or inhibiting CLL cell proliferation by interacting one or more of the GPCRs listed in Tables 1-8, and/or modulating their secondary signaling pathways, such as cAMP pathway, so as to provide a treatment of CLL. The inventive method comprises a step of administering to a CLL patient an effective amount of one or more agents capable of directly or indirectly modulating expression or activity level of one or more GPCRs associated with CLL as listed in Tables 1-8. As used herein, the term "effective amount" of an agent or therapeutic agent is intended to mean a nontoxic but sufficient amount of such therapeutic agents to provide the desired therapeutic effect. The amount that is effective will vary from subject to subject, depending on the age and general condition of the individual, the particular active agent or agents, and the like. Thus, it is not always possible to specify an exact effective amount due to such variations. However, an appropriate effective amount in any individual case may be determined by one of ordinary skill in the art using routine experimentation.

In certain embodiments, the invention provides a novel treatment method and composition for CLL by targets the GPCRs expressed by the CLL cells. GPCR selective agonists and/or antagonists, now known or later developed, and/or antibodies, now known or later developed, that are raised from orphan GPCRs, can be used as therapeutic agents in treating CLL. In certain embodiments, the invention provides that VIP, a VIPR1 agonist, significantly increased apoptosis in aggressive CLL cells and this effect was enhanced by a PDE 4/7 inhibitor, including but not limited to IR284 and ACTH. Thus, the invention provides that VIPR1 is a unique therapeutic target for aggressive CLL. The invention further provides that increasing cAMP with a GPCR agonist in combination with PDE inhibition is a novel therapeutic approach for CLL. Furthermore, the invention provides that LGR8 agonist such as INSL3 protects CLL cells from spontaneous apoptosis. Therefore, the invention provides GPCRs, such as VIPR1, MC2R, and LGR8 are therapeutic targets for CLL, and that these GPCR selective agonists or antagonists are therapeutic agents for treating CLL.

As used herein, the term "modulating" refers to up-regulation, induction, stimulation, potentiation, and/or relief of inhibition, as well as inhibition, attenuation and/or down-regulation or suppression. Inhibitors or antagonists are compounds that, e.g., bind to, partially or totally block stimulation, decrease, prevent, delay activation, inactivate, desensitize, or down regulate genes or proteins of certain interested GPCRs, e.g., VIPR1 activators or agonists are compounds that, e.g., bind to, stimulate, increase, open, activate, facilitate, enhance activation, sensitize, or up regulate gene or proteins of VIPR1.

As used herein, the term "therapeutic agents" may refer to any oligonucleotides (antisense oligonucleotide agents), polynucleotides (e.g. therapeutic DNA), ribozymes, dsRNAs, siRNA, RNAi, and/or gene therapy vectors. The term "antisense oligonucleotide agent" refers to short synthetic segments of DNA or RNA, usually referred to as oligonucleotides, which are designed to be complementary to a sequence of a specific mRNA to inhibit the translation of the targeted mRNA by binding to a unique sequence segment on the mRNA. Antisense oligonucleotides are often developed and used in the antisense technology. The term "antisense technology" refers to a drug-discovery and development technique that involves design and use of synthetic oligonucleotides complementary to a target mRNA to inhibit production of specific disease-causing proteins. Antisense technology permits design of drugs, called antisense oligonucleotides, which intervene at the genetic level and inhibit the production of disease-associated proteins. Antisense oligonucleotide agents are developed based on genetic information.

As an alternative to antisense oligonucleotide agents, ribozymes or double stranded RNA (dsRNA), RNA interference (RNAi), and/or small interfering RNA (siRNA), can also be used as therapeutic agents for regulation of gene expression in cells. As used herein, the term "ribozyme" refers to a catalytic RNA-based enzyme with ribonuclease activity that is capable of cleaving a single-stranded nucleic acid, such as an mRNA, to which it has a complementary region. Ribozymes can be used to catalytically cleave target mRNA transcripts to thereby inhibit translation of target mRNA. The term "dsRNA," as used herein, refers to RNA hybrids comprising two strands of RNA. The dsRNAs can be linear or circular in structure. The dsRNA may comprise ribonucleotides, ribonucleotide analogs, such as 2'-O-methyl ribosyl residues, or combinations thereof. The term "RNAi" refers to RNA interference or post-transcriptional gene silencing (PTGS). The term "siRNA" refers to small dsRNA molecules (e.g., 21-23 nucleotides) that are the mediators of the RNAi effects. RNAi is induced by the introduction of long dsRNA (up to 1-2 kb) produced by in vitro transcription, and has been successfully used to reduce gene expression in variety of organisms. In mammalian cells, RNAi uses siRNA (e.g. 22 nucleotides long) to bind to the RNA-induced silencing complex (RISC), which then binds to any matching mRNA sequence to degrade target mRNA, thus, silences the gene.

As used herein, the therapeutic agents may also include any vectors/virus used for gene therapy. The term "gene therapy" refers to a technique for correcting defective genes or inhibiting or enhancing genes responsible for disease development. Such techniques may include inserting a normal gene into a nonspecific location within the genome to replace a nonfunctional gene; swapping an abnormal gene for a normal gene through homologous recombinants, repairing an abnormal gene to resume its normal function through selective reverse mutation; and altering or regulating gene expression and/or functions of a particular gene. As used herein, a term "vector/virus" refers to a carrier molecule that carries and delivers the "normal" therapeutic gene to the patient's target cells. Because viruses have evolved a way of encapsulating and delivering their genes to human cells in a pathogenic manner, most common vectors for gene therapy are viruses that have been genetically altered to carry the normal human DNA. As used herein, the viruses/vectors for gene therapy include retroviruses, adenoviruses, adeno-associated viruses, and herpes simplex viruses. The term "retrovirus" refers to a class of viruses that can create double-stranded DNA copies of their RNA genomes, which can be further integrated into the chromosomes of host cells, for example, Human immunodeficiency virus (HIV) is a retrovirus. The term "adenovirus" refers to a class of viruses with double-stranded DNA genomes that cause respiratory, intestinal, and eye infections in humans, for instance, the virus that cause the common cold is an adenovirus. The term "adeno-associated virus" refers to a class of small, single-stranded DNA viruses that can insert their genetic material at a specific site on chromosome 19. The term "herpes simplex viruses" refers to a class of double-stranded DNA viruses that infect a particular cell type, neurons. Herpes simplex virus type 1 is a common human pathogen that causes cold sores.

In certain preferred embodiments, the present invention provides a method of treating CLL using protein inhibitors, ligands, and/or antagonists and their pharmaceutical compositions that directly or indirectly alter certain GPCRs mRNA and protein expressions or activity in CLL cells. Such GPCR selective inhibitors, ligands, antagonists comprise any polypeptides, proteins, synthetic, non-toxic, bioactive molecules, and/or immunologically active molecules that are capable of directly or indirectly inhibiting lymphocyte proliferation or promoting cell death by binding to certain GPCR gene and/or protein and inhibiting the cAMP catabolism resulting in elevation of intracellular cAMP levels, and apoptosis of CLL lymphocytes. As used herein, the term "pharmaceutical composition" contemplates compositions comprising one or more therapeutic agents as described above, and one or more pharmaceutically acceptable carriers or vehicles. As used herein, the term "pharmaceutically acceptable carriers or vehicles" comprises any acceptable materials, and/or any one or more additives known in the art. As used herein, the term "carriers" or "vehicle" refer to carrier materials suitable for drug administration through various conventional administration routes known in the art. Carriers and vehicles useful herein include any such materials known in the art, which are nontoxic and do not interact with other components of the composition in a deleterious manner.

The present invention also contemplates any conventional methods for formulation of pharmaceutical compositions as described above. Various additives, known to those skilled in the art, may be included in the formulations. For example, solvents, including relatively small amounts of alcohol, may be used to solubilize certain drug substances. Other optional additives include opacifiers, antioxidants, fragrance, colorant, gelling agents, thickening agents, stabilizers, surfactants and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

Throughout this application, various publications are referenced. The disclosures of all of these publications and those references cited within those publications in their entireties are hereby incorporated by reference into this application in order to more fully describe the state of the art to which this invention pertains.

Several examples are presented below. It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

The present description is further illustrated by the following examples, which should not be construed as limiting in any way. It is apparent for skill artisans that various modifications and changes are possible and are contemplated within the scope of the current invention. The contents of all cited references (including literature references, issued patents, or published patent applications as cited throughout this application) are hereby expressly incorporated by reference.

EXAMPLE

Example 1

Materials and Methods

Materials:

Blood was collected from healthy donors and CLL patients and PBMCs were isolated using standard techniques. Normal B-cells were enriched from healthy donor PBMCs using standard positive and/or negative selection techniques.

IR284, (4-(3-chloro-4-methoxyphenyl)-2-(1-morpholine-4-carbonyl)piperadin-4-yl)-4a,5,8,8a-tetrahydrophthalazin-1(2H)-one was custom synthesized by the UCSD Cancer Center Medicinal Chemistry Core and was used at 100 nM for the experiments presented.

VIP (vasoactive intestinal peptide receptor agonist) was purchased from Tocris Bioscience, (Minneapolis, Minn.) and used at 1 µM in the experiments presented.

ACTH (a melanocortin 2 receptor [MC2R] agonist) was purchased from GenWay, (San Diego, Calif.) and used at 1 nM in the presented experiments.

Methods:

Real-Time PCR Confirmation of VIPR and MC2R Receptor mRNA Expression:

Primers for GPCRs were designed using the NCBI Entrez search engine.

All primers were obtained from ValueGene (San Diego, Calif.) and diluted with diethyl pyrocarbonate-(DPEC)-treated water to a stock concentration of 200 µM.

RNA was extracted from 2 million CLL-cells or normal PBMC using a commercial kit according to the manufacturer's instructions and reverse-transcribed to cDNA using an Applied Biosystems cDNA synthesis kit, per the manufacturer's instructions. Real-time PCR was conducted using a SybrGreen mastermix (Eurogentec, San Diego, Calif.). Data are presented using the relative cycle threshold ($\Delta C_t$) method, normalizing to 28S rRNA. For real-time PCR, the threshold for receptor detection was a $\Delta C_t$ value of approximately 32; GPCRs with $\Delta C_t$ values of >32 were considered as not expressed.

Complementary DNA (cDNA) isolated from normal (n=10), indolent (n=10), and aggressive B-cells (n=10) was run on a human GPCR-specific array. The array defined the mRNA expression of 355 non-chemosensory GPCRs using comparative cycle threshold ($C_t$) values. The results were classified by G-protein linkage and were validated by real-time PCR and fluorescence activated cell sorting, to assay apoptosis.

A real-time GPCR array can identify mRNA for all known non-chemosensory human GPCRs (n=355). The use of this GPCR array with samples from patients with indolent and aggressive CLL provided novel profiles (including individual and multiple GPCRs) in these patient samples. Validation of the array by independent real-time PCR analyses confirms their expression, as does protein expression (in some cases), followed by assessment of effects of receptor activation and blockade on second messenger generation and CLL cell growth and death. Available drugs are tested for GPCRS with known agonists but for orphan GPCRs, antibodies are developed and used to perturb cell function and promote CLL cell death (in studies with CLL cells in culture or in experimental animals).

cAMP Accumulation Assay:

A standard cAMP radioimmunoassay was used to assess cAMP accumulation. One million CLL-cells or normal PBMC/ml in RPMI 1540 buffer+10% FBS were plated in a 12-well cell culture plate and incubated for 20 min at 37° C. in air plus 5% $CO_2$ with a dual PDE4/7 inhibitor (IR284). VIP or ACTH were then added to the 12-well culture plate and incubated for 10 min at 37° C. in air plus 5% $CO_2$. The cells were then centrifuged at 1200 rpm for 5 min at 4° C. The media was aspirated and 50 µl of 7.5% trichloroacetic acid (TCA) was added to each cell pellet to release cAMP from the cells. The TCA-suspended sample was diluted in 1 ml 10 mM sodium acetate and acetylated with 20 ul triethylamine and 10 ul acetic anhydride. The competitive binding assay consists of 50 µl of diluted, acetylated sample, 25 µl AMP antibody and 25 µl $^{125}$I-labeled cAMP (Perkin Elmer). Following overnight incubation, 50 µl secondary antibody was added to each reaction and incubated for 1 h at 4° C. Three washes with 12% polyethylene glycol in 10 mM sodium acetate pH 6.2 were performed and the samples transferred to fresh assay tubes for detection of gamma radiation using a WIZARD2 Automatic Gamma Counter (PerkinElmer).

Assay of Cellular Apoptosis:

Flow cytometry was used to detect annexin V/fluorescein isothiocyanate (FITC) and propidium iodide (PI) staining to determine the apoptotic population of treated cells. CLL-cells or normal PBMC (1,000,000/ml) in RPMI 1540+10% FBS were incubated for 48 hr in standard culture conditions with or without drugs and then assayed for annexinV/PI staining per manufacturer's protocol using a FACScan (Becton Dickinson Biosciences, San Jose, Calif.) flow cytometer.

Example 2

Disease Stage Specific G Protein-Coupled Receptor Expression in Clinical Disorder: Chronic Lymphocytic Leukemia as a Model This example demonstrates that altered GPCR expression is disease stage-specific, using CLL as a model, and can serve as a both biomarkers and targets for CLL. Using a TaqMan GPCR array altered GPCR expression was identified in normal B-cells and CLL cells from both aggressive and indolent patients. It was found normal B-cells (n=5) to express 200 GPCRs, 74 of which were orphan receptors. In contrast, indolent CLL (n=5) express 170 GPCR's, 74 of which were orphans and aggressive CLL (n=5) express 117 GPCR's, 51 of which were orphan. Comparing the expression of GPCRs, it was found that not only a number of GPCRs either uniquely expressed or altered with CLL, but also that their expression differed between the stages of the disease. Of interest, vasoactive intestinal polypeptide receptor 1 (VIPR1), a Gs-coupled GPCR, increased 706-fold in aggressive CLL compared to indolent and VIP induced apoptosis of CLL cells (P<0.05, n=3). These data indicate that GPCR expression provided stage-specific therapeutic targets, in particular as a treatment in the management of CLL.

Table 1 below provides a listing of the 170 GPCRs expressed in indolent CLL cells (See FIG. 1). Linkages of GPCRs to G-proteins or classification as Orphan receptors were determined by the available literature at the time of filing of the provisional patent. The most recent linkage classifications and in addition, ligands/drugs for each receptor can be found in the GPCR database maintained by the International Union of Basic and Clinical Pharmacology and the British Pharmacological Society, the *IUPHAR/BPS Guide to Pharmacology*.

TABLE 1

Alphabetical listing of the 170 GPCRs expressed in Indolent CLL cells

| Orphans | Gs-linked | Gi-linked | Non Gs/Gi-linked |
|---|---|---|---|
| BAI1 | ADORA2A | ADORA3 | AVPR1B |
| BAI2 | ADRB1 | ADRA2A | BDKRB1 |
| CCRL2 | ADRB2 | AGTRL1 | CHRM3 |
| CD97 | AVPR2 | BDKRB1 | CHRM5 |
| CELSR1 | DRD1 | BLR1 | CYSLTR1 |
| CELSR2 | DRD5 | C3AR1 | CYSLTR2 |
| CELSR3 | GIPR | C5R1 | EDG4 |
| CMKLR1 | GPBAR1 | CCR10 | EDG5 |
| ELTD1 | MC1R | CCR3 | EDG7 |
| EMR1 | MC2R | CCR4 | F2RL3 |
| EMR2 | MC3R | CCR6 | FZD10 |
| EMR3 | MC4R | CCR7 | FZD1 |
| GPR101 | MC5R | CHRM2 | FZD2 |
| GPR10 | P2RY11 | CHRM4 | FZD3 |
| GPR113 | P2RY5 | CNR1 | FZD5 |
| GPR114 | PTGER4 | CNR2 | FZD7 |
| GPR115 | PTGIR | CXCR3 | FZD8 |
| GPR120 | VIPR1 | CXCR4 | FZD9 |
| GPR125 | | EBI2 | GHSR |
| GPR12 | | EDG1 | GPR21 |
| GPR141 | | EDG3 | GPR23 |
| GPR146 | | EDG6 | GPR40 |
| GPR148 | | EDG7 | GPR43 |
| GPR150 | | F2RL3 | GPR92 |
| GPR152 | | FPRL2 | HRH2 |
| GPR153 | | GABBR1 | LTB4R |
| GPR15 | | GAL2R | LTB4R2 |
| GPR160 | | GPR18 | OXTR |
| GPR171 | | GPR23 | P2RY1 |
| GPR173 | | GPR81 | P2RY4 |
| GPR174 | | GRM2 | PTAFR |
| GPR19 | | HTR1A | TAAR2 |
| GPR1 | | HTR1B | TBXA2R |
| GPR20 | | HTR1D | |
| GPR22 | | HTR1E | |
| GPR25 | | HTR1F | |
| GPR31 | | NPY1R | |
| GPR32 | | OPRL1 | |
| GPR45 | | OXER1 | |
| GPR4 | | P2RY13 | |

TABLE 1-continued

Alphabetical listing of the 170 GPCRs expressed in Indolent CLL cells

| Orphans | Gs-linked | Gi-linked | Non Gs/Gi-linked |
|---|---|---|---|
| GPR52 | | P2RY14 | |
| GPR55 | | PPYR1 | |
| GPR61 | | RLN3R1 | |
| GPR62 | | SSTR1 | |
| GPR68 | | SSTR2 | |
| GPR75 | | SSTR3 | |
| GPR82 | | XCR1 | |
| GPR83 | | | |
| GPR84 | | | |
| GPR88 | | | |
| GPR97 | | | |
| GPRC5A | | | |
| GPRC5D | | | |
| LGR4 | | | |
| LGR6 | | | |
| LPHN1 | | | |
| MAS1 | | | |
| MAS1L | | | |
| MRGPRE | | | |
| MRGPRX1 | | | |
| MRGPRX2 | | | |
| MRGPRX3 | | | |
| MRGPRX4 | | | |
| OPN3 | | | |
| OXGR1 | | | |
| P2RY10 | | | |
| P2RY8 | | | |
| TAAR5 | | | |
| TAAR6 | | | |
| TAAR8 | | | |
| TAAR9 | | | |
| TM7SF1 | | | |

Table 2 provides a listing of the 117 GPCRs expressed in aggressive CLL cells. Linkages of GPCRs to G-proteins or classification as Orphan receptors were determined by the available literature at the time of filing of the provisional patent. The most recent linkage classifications and in addition, ligands/drugs for each receptor can be found in the GPCR database maintained by the International Union of Basic and Clinical Pharmacology and the British Pharmacological Society, the *IUPHAR/BPS Guide to Pharmacology*.

TABLE 2

Alphabetical listing of the 117 GPCRs expressed in Aggressive CLL cells

| Orphans | Gs-linked | Gi-linked | Non Gs/Gi-linked |
|---|---|---|---|
| BAI1 | ADORA2A | ADRA2B | AVPR1B |
| CCRL2 | ADORA2B | BDKRB1 | BDKRB1 |
| CD97 | ADRB1 | BLR1 | CYSTLR1 |
| CELSR1 | ADRB2 | C5R1 | EDG4 |
| CELSR3 | DRD1 | CCR10 | EDG5 |
| EMR1 | DRD5 | CCR3 | FZD10 |
| GPR113 | GIPR | CCR6 | FZD1 |
| GPR120 | MC1R | CCR7 | FZD2 |
| GPR135 | MC2R | CHRM4 | FZD3 |
| GPR141 | MC4R | CNR2 | FZD5 |
| GPR146 | MC5R | CXCR3 | FZD7 |
| GPR148 | P2RY11 | CXCR4 | FZD8 |
| GPR152 | P2RY5 | EBI2 | GPR21 |
| GPR153 | PTGER4 | EDG1 | GPR40 |
| GPR15 | VIPR1 | EDG3 | GPR43 |
| GPR160 | | EDG6 | GPR56 |
| GPR171 | | FPRL2 | GPR92 |
| GPR174 | | GABBR1 | HRH2 |
| GPR21 | | HTR1B | LTB4R |
| GPR22 | | HTR1D | LTB4R2 |
| GPR25 | | NPY1R | PTAFR |

TABLE 2-continued

Alphabetical listing of the 117 GPCRs expressed in Aggressive CLL cells

| Orphans | Gs-linked | Gi-linked | Non Gs/Gi-linked |
|---|---|---|---|
| GPR32 | | OPRL1 | TBXA2R |
| GPR34 | | OXER1 | |
| GPR35 | | P2RY13 | |
| GPR40 | | P2RY14 | |
| GPR43 | | PPYR1 | |
| GPR45 | | RLN3R1 | |
| GPR4 | | SSTR1 | |
| GPR52 | | SSTR3 | |
| GPR56 | | | |
| GPR63 | | | |
| GPR65 | | | |
| GPR68 | | | |
| GPR7 | | | |
| GPR82 | | | |
| GPR83 | | | |
| GPR8 | | | |
| GPR92 | | | |
| HTR7 | | | |
| LGR4 | | | |
| LGR6 | | | |
| OPN3 | | | |
| OR2A4 | | | |
| OR2C3 | | | |
| P2RY10 | | | |
| P2RY8 | | | |
| TAAR5 | | | |
| TAAR8 | | | |
| TM7SF1 | | | |
| VN1R1 | | | |
| VN1R2 | | | |

Figure 2:
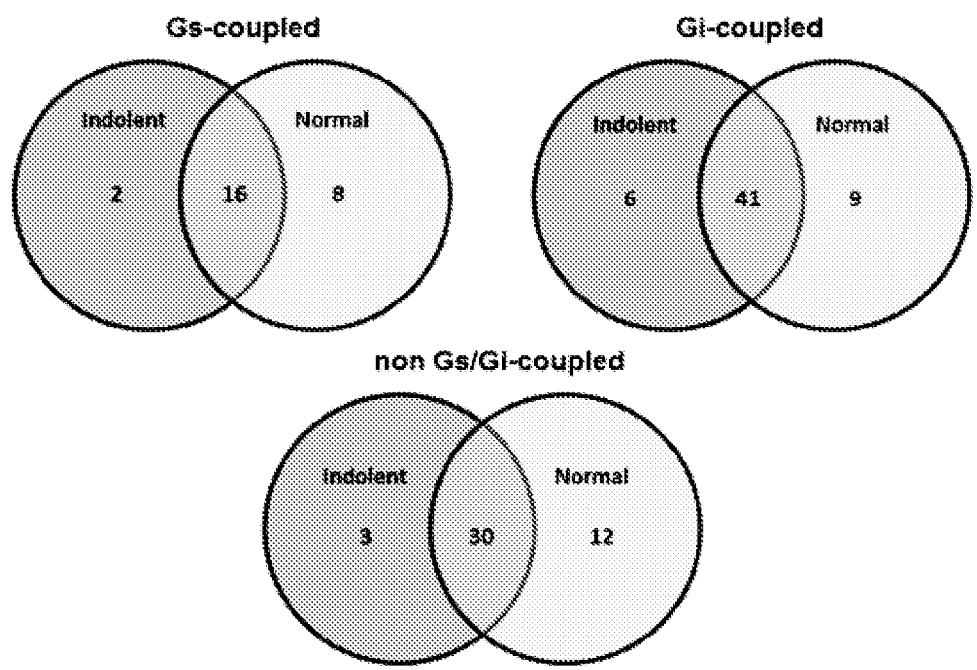
FIG. 2 is a venn diagram showing comparisons of numbers of GPCR genes that are expressed in normal B-cells vs indolent CLL.

Table 3 provides a list of GPCRs that are uniquely expressed in indolent CLL cells as compared to normal B-cells (See FIG. 2). One of the Gs-coupled GPCR MC2R is also uniquely expressed in aggressive CLL as compared to normal B-cell.

| Gs-coupled | Gi-coupled | Non-Gs/Gi-coupled |
|---|---|---|
| AVPR2 | ADORA3 | TACR2 |
| MC2R | CNR1 | EDG7 |
| | EDG7 | F2RL3 |
| | F2RL3 | |
| | HTR1E | |
| | HTR1F | |

Table 4 provides a listing of GPCRs with significantly lower (2-fold or lower, i.e. 50% or less) mRNA expression in indolent CLL cells as compared to normal B-cells

| | Fold Difference (Indolent vs. Normal) |
|---|---|
| C5R1 | −67.0 |
| P2RY13 | −63.0 |
| GPR35 | −25.8 |
| FPRL2 | −12.4 |
| PTAFR | −8.7 |
| EDG1 | −7.4 |
| GPR15 | −6.6 |
| EDG5 | −5.0 |
| CCR7 | −5.0 |
| CCR4 | −4.7 |
| EMR1 | −4.3 |
| TM7SF1 | −4.1 |
| FZD9 | −3.5 |
| GPR18 | −3.4 |
| C3AR1 | −3.4 |
| GALR2 | −3.2 |

-continued

| | Fold Difference (Indolent vs. Normal) |
|---|---|
| NPY6R | -3.0 |
| P2RY5 | -2.9 |
| GRM2 | -2.7 |
| GPR43 | -2.7 |
| BDKRB1 | -2.5 |
| GPR3 | -2.2 |
| P2RY11 | -2.0 |

(N=23) in related to the venn diagram in FIG. 2.

Table 5 provides genes of GPCRs and others with significantly higher (2-fold or greater, i.e., 200% or greater) mRNA expression in indolent CLL cells as compared to normal B-cells (N=7) in related to venn diagram in FIG. 2.

| | Fold Difference (Indolent vs. Normal) |
|---|---|
| AGTRL1 | 121.0 |
| AVPR1B | 40.9 |
| RLN3R1 | 26.8 |
| SSTR3 | 14.7 |
| GPR34 | 13.6 |
| P2RY4 | 11.0 |
| GPR81 | 10.8 |
| GPR173 | 10.3 |
| LGR4 | 9.7 |
| LGR6 | 8.8 |
| MC5R | 8.6 |
| MAS1 | 8.3 |
| CNR2 | 8.2 |
| VN1R1 | 7.4 |
| FZD3 | 7.3 |
| FZD5 | 6.6 |
| HTR1B | 6.5 |
| HTR1D | 6.2 |
| GPR45 | 5.9 |
| HMBS | 5.9 |
| DRD5 | 5.8 |
| GPR20 | 5.7 |
| GPR32 | 5.5 |
| GPR82 | 5.5 |
| GPR61 | 5.0 |
| EBI2 | 5.0 |
| CELSR3 | 4.9 |
| MRGPRX3 | 4.5 |
| GPR148 | 4.1 |
| GPR7 | 4.0 |
| TBXA2R | 4.0 |
| C11ORF4 | 3.9 |
| TAAR8 | 3.7 |
| CHRM3 | 3.7 |
| TRBV5 | 3.7 |
| ADORA2A | 3.7 |
| HTR1A | 3.5 |
| XCR1 | 3.5 |
| PHGDH | 3.5 |
| ADRB2 | 3.4 |
| SSTR2 | 3.4 |
| CCR10 | 3.4 |
| CELSR1 | 3.4 |
| MC4R | 3.3 |
| FKSG83 | 3.2 |
| HDAC3 | 3.1 |
| GABBR1 | 3.1 |
| CHRM2 | 3.0 |
| MRGPRE | 3.0 |
| OXER1 | 3.0 |
| GPR52 | 2.9 |
| MC3R | 2.9 |
| CCR3 | 2.7 |
| SENP3 | 2.6 |
| CHRM4 | 2.6 |
| FZD2 | 2.6 |
| GPR55 | 2.6 |
| GPR92 | 2.5 |
| GPR12 | 2.5 |
| P2RY14 | 2.5 |
| ADRA2A | 2.4 |
| GUSB | 2.4 |
| CYSLTR1 | 2.3 |
| IPO8 | 2.3 |
| B2M | 2.3 |
| PPIA | 2.3 |
| P2RY10 | 2.3 |
| MC1R | 2.2 |
| PTGER4 | 2.2 |
| GAPDH | 2.2 |
| DRD1 | 2.2 |
| GPR23 | 2.1 |
| LANCL1 | 2.1 |
| RPLP0 | 2.1 |
| OR7C2 | 2.1 |
| VN1R5 | 2.0 |
| BLR1 | 2.0 |

Figure 3:
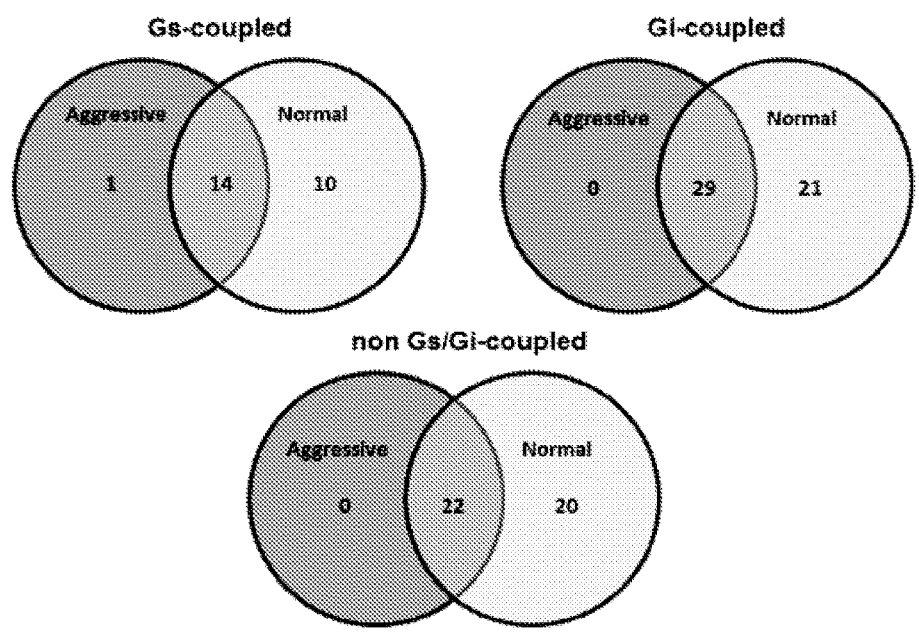
FIG. 3 is a venn diagram showing comparison of numbers of GPCR genes (Gs-coupled and Gi-coupled) that are expressed in normal B-cells vs aggressive CLL.

Table 6 provides GPCRs with significantly lower (2-fold or lower, i.e., 50% or less) mRNA expression in aggressive CLL cells as compared to normal B-cells (N=38) in related to venn diagram in FIG. 3.

| | Fold Difference (Aggressive vs. Normal) |
|---|---|
| C5R1 | -47.2 |
| P2RY13 | -37.7 |
| GPR35 | -31.7 |
| GPR15 | -25.6 |
| ADORA2B | -24.9 |
| GPR153 | -21.2 |
| GPR146 | -18.5 |
| GPR65 | -17.7 |
| GPR56 | -14.9 |
| GPR141 | -10.8 |
| GPR8 | -9.4 |
| P2RY5 | -8.9 |
| EDG5 | -7.5 |
| GPR40 | -7.3 |
| HRH2 | -7.1 |
| CCR6 | -5.8 |
| PTAFR | -5.3 |
| GPR25 | -5.2 |
| ADRA2B | -5.2 |
| EDG1 | -5.0 |
| FPRL2 | -5.0 |
| LTB4R2 | -4.3 |
| GPR68 | -4.2 |
| EDG3 | -4.2 |
| CCR3 | -4.0 |
| FZD8 | -3.6 |
| CCRL2 | -3.0 |
| CCR7 | -2.8 |
| PPYR1 | -2.8 |
| NPY6R | -2.7 |
| BDKRB1 | -2.6 |
| GPR160 | -2.5 |
| OR2A4 | -2.2 |
| P2RY11 | -2.2 |
| ADRB1 | -2.1 |
| EMR1 | -2.1 |
| GPR152 | -2.1 |
| OPRL1 | -2.0 |

Table 7 provides a listing of genes of GPCRs and others with significantly higher (2-fold or greater, i.e. 200% or greater) mRNA expression in Aggressive CLL cells compared to Normal B-cells (N=44) in related to the venn diagrams in FIG. 3.

|  | Fold Difference (Aggressive vs. Normal) |
| --- | --- |
| FZD3 | 33.5 |
| AVPR1B | 27.2 |
| LGR6 | 24.5 |
| P2RY14 | 20.4 |
| VIPR1 | 19.5 |
| LGR4 | 10.0 |
| CNR2 | 8.8 |
| SSTR3 | 7.8 |
| CELSR3 | 7.7 |
| GPR82 | 6.5 |
| FZD5 | 6.4 |
| TBXA2R | 5.9 |
| MC5R | 5.8 |
| GPR7 | 5.1 |
| VN1R1 | 4.9 |
| RLN3R1 | 4.6 |
| GPR34 | 4.6 |
| ADORA2A | 4.5 |
| HMBS | 4.4 |
| HDAC3 | 4.4 |
| TAAR8 | 4.2 |
| TRBV5 | 3.5 |
| IPO8 | 3.4 |
| MC1R | 3.3 |
| CELSR1 | 3.2 |
| P2RY10 | 3.1 |
| PPIA | 3.1 |
| CCR10 | 3.1 |
| C11ORF4 | 3.0 |
| ADRB2 | 3.0 |
| GPR171 | 3.0 |
| OPN3 | 3.0 |
| B2M | 2.9 |
| GPR52 | 2.8 |
| LANCL1 | 2.7 |
| GUSB | 2.6 |
| SENP3 | 2.6 |
| GABBR1 | 2.4 |
| GPR45 | 2.4 |
| CHRM4 | 2.3 |
| GPR92 | 2.2 |
| RPLP0 | 2.2 |
| LANCL2 | 2.2 |
| HTR1B | 2.1 |

Figure 4:
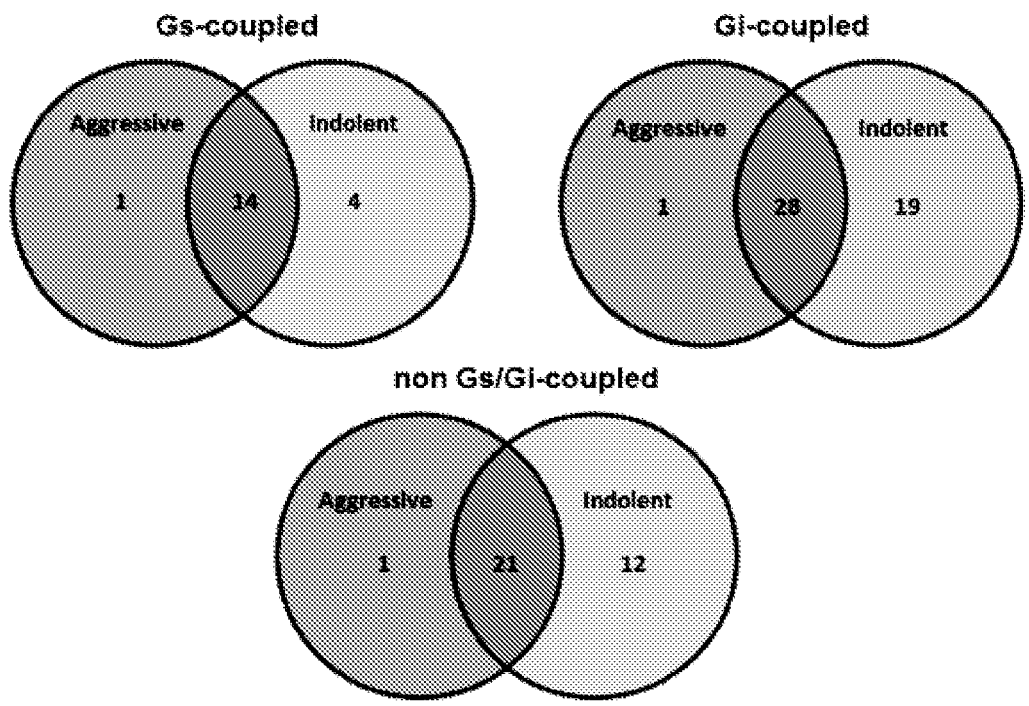
FIG. 4 is a venn diagram showing comparison of numbers of GPCR genes (Gs-coupled and Gi-coupled) that are expressed in indolent CLL vs aggressive CLL.

Table 8 provides a listing of GPCRs uniquely expressed in aggressive CLL, as well as in indolent CLL, in related to the venn diagrams in FIG. 4.

| Gs-coupled | Gi-coupled | Non Gs/Gi-coupled | Gs-coupled | Gi-coupled | Non Gs/Gi-coupled |
| --- | --- | --- | --- | --- | --- |
| ADORA2B | ADRA2B | GPR56 | AVPR2 | ADORA3 | CHRM3 |
|  |  |  | GPBAR1 | ADRA2A | CHRM5 |
|  |  |  | MC3R | AGTRL1 | CYSLTR2 |
|  |  |  | PTGIR | C3AR1 | EDG7 |
|  |  |  |  | CCR4 | F2RL3 |
|  |  |  |  | CHRM2 | FZD9 |
|  |  |  |  | CNR1 | GHSR |
|  |  |  |  | EDG7 | GPR23 |
|  |  |  |  | F2RL3 | OXTR |
|  |  |  |  | GALR2 | P2RY1 |
|  |  |  |  | GPR18 | P2RY4 |
|  |  |  |  | GPR23 | TAAR2 |
|  |  |  |  | GPR81 |  |
|  |  |  |  | GRM2 |  |
|  |  |  |  | HTR1A |  |
|  |  |  |  | HTR1E |  |
|  |  |  |  | HTR1F |  |
|  |  |  |  | SSTR2 |  |
|  |  |  |  | XCR1 |  |

Example 3

VIPR1 is a Biomarker and Therapeutic Target in CLL

Figure 5:
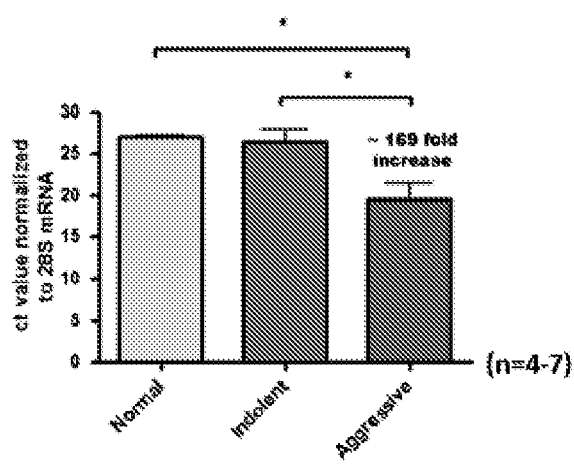
FIG. 5 illustrates VIPR1 mRNA expression in normal B-cells (n=4), indolent CLL (n=5), and aggressive CLL (n=7), as determined by real-time PCR. Cycle thresholds (lower value denotes higher expression) normalized to 28S rRNA. Significance was determined by Student's t-test (* connotes P<0.05).
Figure 6:
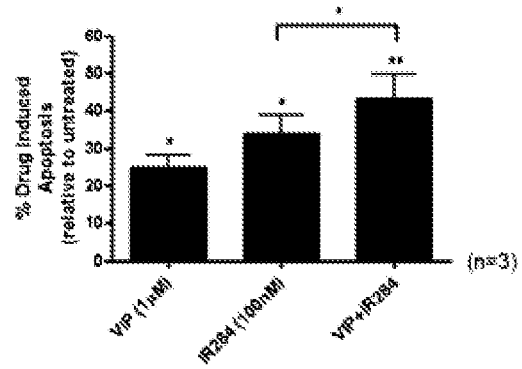
FIG. 6 illustrates cAMP accumulation in aggressive CLL cells in response to treatment with 1 μM VIP+100 nM IR284 (n=8). The results are expressed relative to cAMP levels in cells treated only with 100 nM IR284, a PDE4/7 inhibitor. Statistical significance was determined by paired t test and is shown (*=P<0.05) compared to cells treated only with IR284.
Figure 7:
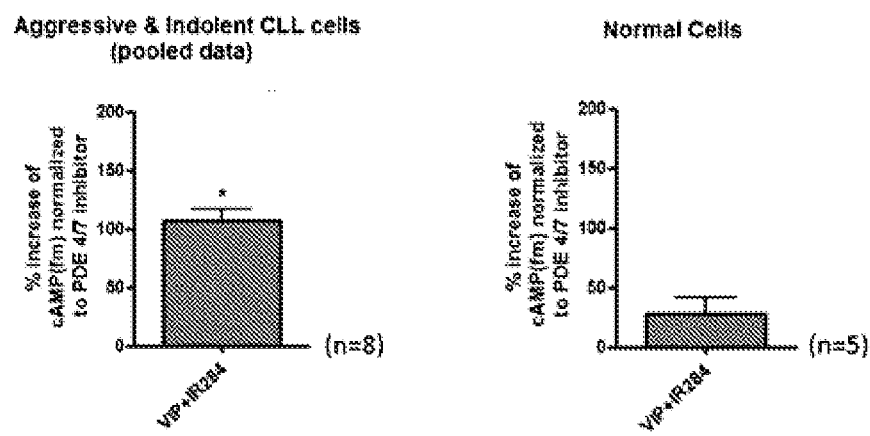
FIG. 7 illustrates apoptosis of CLL cells (data from Aggressive and Indolent CLL cells), left panel, and normal B-cells (n=3), right panel, in response to 1 μM VIP+100 nM IR284. Statistical significance, determined by Student's t-test, is shown (*=P<0.05) compared to cells treated only with 100 nM IR284.
Figure 8:
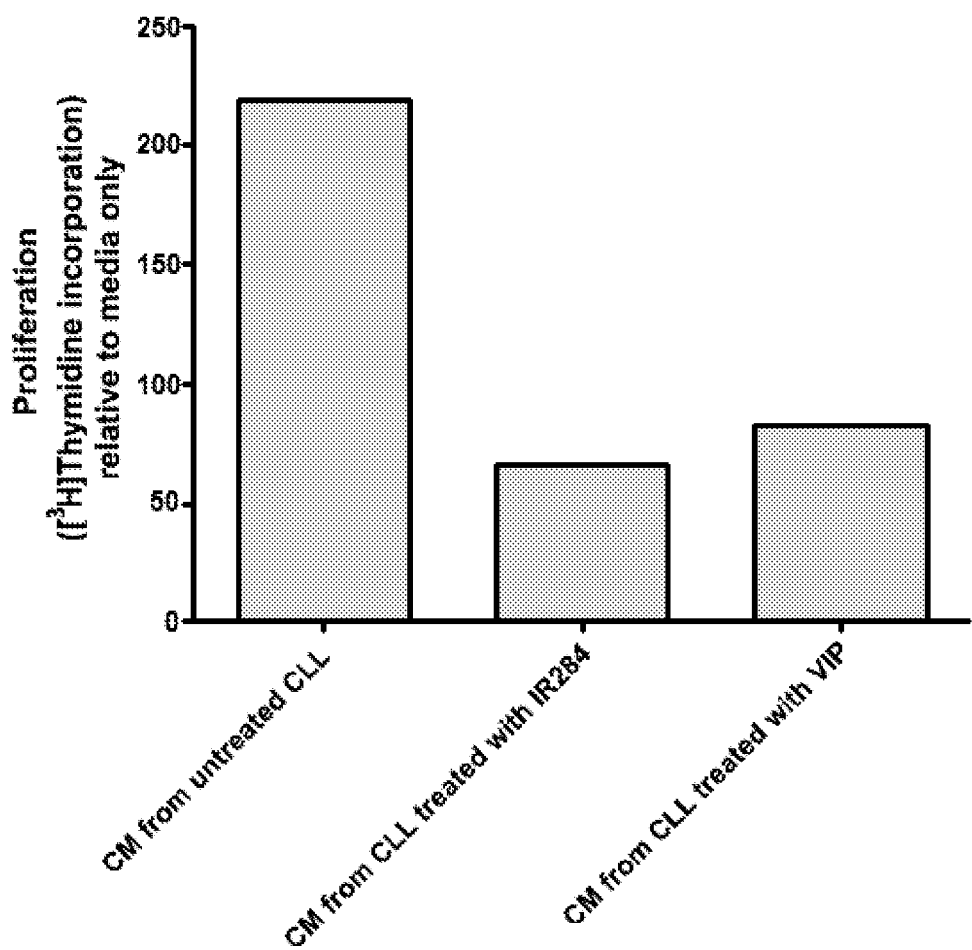
FIG. 8 illustrates that treatment with IR284 or VIP suppressed proliferation of the stromal microenvironment in the conditioned media from indolent CLL. Mononuclear cells derived from the blood of Indolent CLL patients were grown in tissue culture media (RPMI 1640+10% Heat-Inactivated Fetal Bovine Serum) and incubated for 24 hr in the absence of any drug ("untreated CLL"), in the presence of the phosphodiesterase 4/7 inhibitor IR284 (100 nM) or the VIPR agonist VIP (1 mM). In the 24 hr incubation period products excreted from the cells in response to the treatments accumulate in the media, which is called "conditioned media" (CM). CM was harvested from the cell cultures by subjecting them to centrifugation at 233 rcf for 10 minutes at 4° C. to pellet cells and debris. The liquid portion was removed and used as CM. To assess the impact of CM from the indolent CLL cultures upon the proliferation of bone marrow-derived stromal cells (which make up the supportive microenvironment of CLL in vivo), CM was added to NK.tert bone marrow-derived stromal cells along with [3H] thymidine to assess DNA synthesis/cell proliferation
Figure 9A:
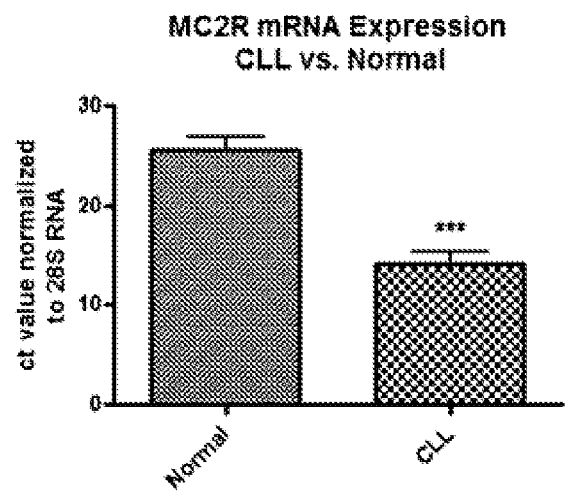
FIG. 9A shows MC2R mRNA expression in normal B-cells (n=9) and CLL cells (n=9) as determined by real-time PCR. Cycle thresholds (lower value denotes higher expression) normalized to 28S. Statistical significance was determined by Student's t-test and is depicted by (***) for P<0.001 compared to normal.
Figure 9B:
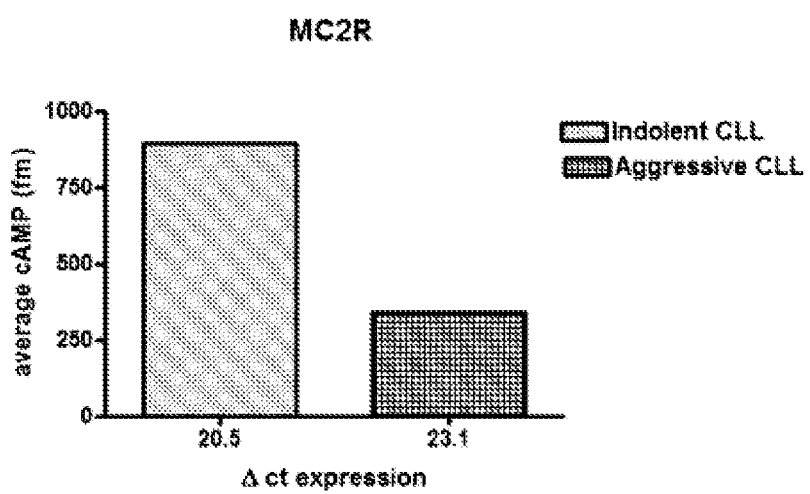
FIG. 9B shows cAMP accumulation in indolent CLL cells (n=4) and aggressive CLL cells (n=5) in response to treatment with 1 nM ACTH+100 nM IR284. Statistical significance was determined by paired t test with (*) P<0.05 compared to IR284 alone.
Figure 9C:
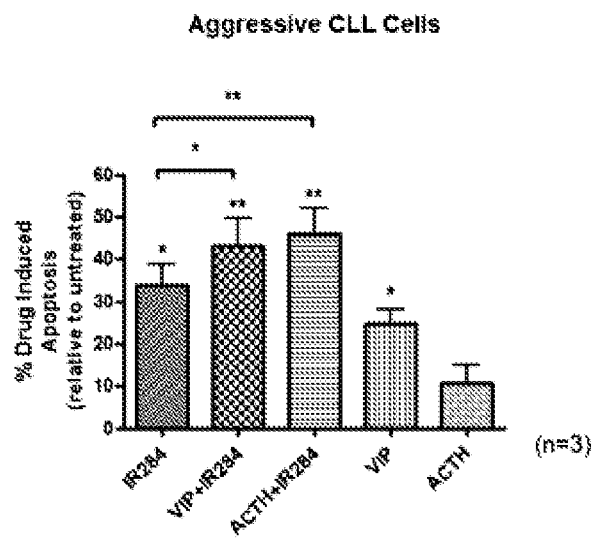
FIG. 9C shows that when used in combination with PDE inhibitor IR284 (100 nM), ACTH (1 nM) and VIP (1 mM) increase apoptosis in Aggressive CLL cells above IR284 alone (**=P<0.01).

This example demonstrates that VIPR1 mRNA expression is increased in indolent CLL (n=5), as well as significantly increased in aggressive CLL (n=7), as compared to that in normal B-cells (n=4), as determined by real-time PCR (See FIG. 5, and Table 9 below). This example also demonstrates that VIP increases apoptosis in aggressive CLL cells, but does not promote apoptosis in normal B-cells. The increased cAMP and apoptosis effect of VIP is significantly enhanced with a cyclic AMP phosphodiesterase 4/7 inhibitor, IR284 (See FIGS. 6 & 7). Furthermore, this example demonstrates that treatment with IR284 or VIP suppressed proliferation of the stromal microenvironment in the conditioned media from indolent CLL (See FIG. 8).

TABLE 9

Vasoactive intestinal peptide receptor 1 (VIPR1) displays the greatest increase in expression between the two stages of CLL

| Indolent vs. Normal | | Aggressive vs. Normal | | Aggressive vs. Indolent | |
| --- | --- | --- | --- | --- | --- |
| GPCR | ΔΔct | GPCR | ΔΔct | GPCR | ΔΔct |
| EDG7 (LPA receptor 3) $G_i$ | 8.0 (262 fold-increase) | VIPR1 (vasoactive intestinal peptide) $G_s$ | 4.5 (22 fold-increase) | VIPR1 (vasoactive intestinal peptide) $G_s$ | 9.5 (706 fold-increase) |

Example 4

MC2R is a Biomarker and Therapeutic Target in CLL

This example demonstrates differences in MC2R mRNA expression between CLL patient cells and normal B-cells and levels of mRNA expression in CLL subtypes reflect cAMP production in response to ACTH. In addition, both VIP and ACTH promote apoptosis of aggressive CLL cells.

Example 5

LGR8 is a Biomarker and Therapeutic Target in CLL

LGR8 is a G protein-coupled receptor (GPCR) that affects testicular descent and is also known as GPR106, Leucine-rich repeat G protein-coupled receptor 8, or Relaxin receptor2 (Rxfp2), similar to G protein-coupled receptor affecting testicular descent (*H. sapiens*). The peptide hormone insulin-like peptide 3 (INSL3) is essential for testicular descent and has been implicated in the control of adult fertility in both sexes. The human INSL3 receptor LGR8, binds INSL3. If transfected into 293T cells, recombinant LGR8 stimulated with INSL3 activates adenylyl cyclase and increases accumulation of intracellular cAMP (*J Biol Chem* 277: 31283-31286, 2002; *Science*, 295: 637-638, 2002).

In germ cells, INSL3 binds LGR8 and activates the inhibitory G protein, Gi, leading to decreases in cAMP production. Treatment with INSL3 initiates meiotic progression of arrested oocytes in preovulatory follicles in vitro and in vivo and suppresses male germ cell apoptosis in vivo.

Figure 10:
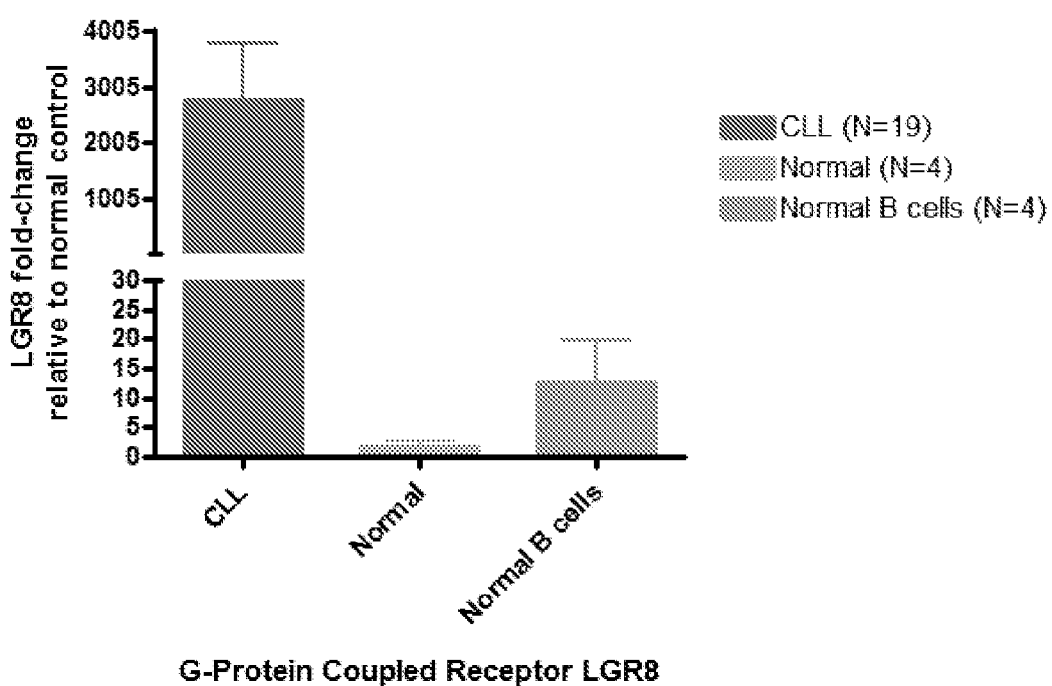
FIG. 10 illustrates that CLL cells express more LGR8 mRNA than do normal peripheral blood mononuclear cells or normal B cells. The mRNA studies were undertaken using RT-PCR with primers specific for LGR8 and involved the preparation of peripheral blood mononuclear cells (PBMC) from CLL patients (n=19), normal subjects (n=4) and of B cells (n=4) from the PBMC of normal subjects. The data indicate much higher expression of LGR8 in the samples from patients with B cell CLL and that this higher level of expression cannot be attributed to the higher expression of LGR8 in B cells.
Figure 11:
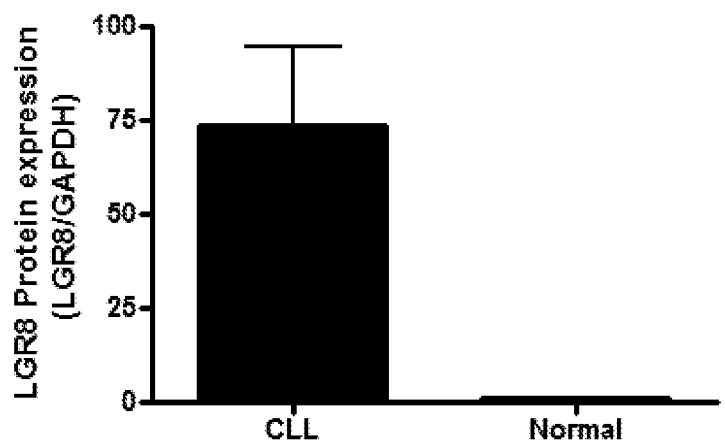
FIG. 11 shows data from immunoblot studies using LGR8 antibody (ab43431) from Abcam and document that more LGR8 protein is expressed by CLL cells.
Figure 12:
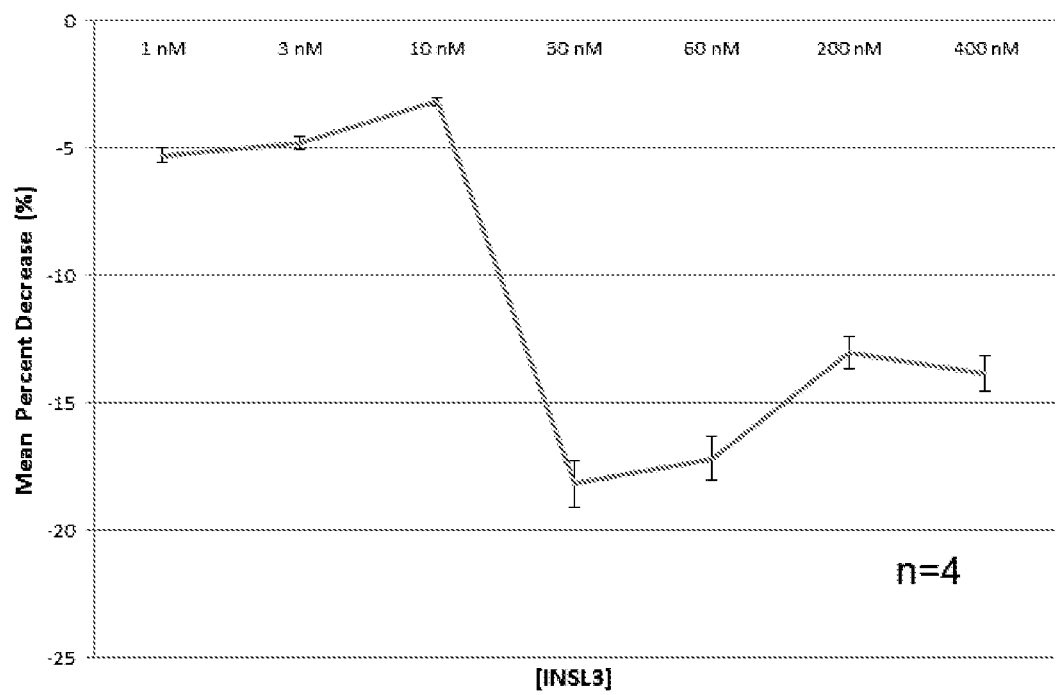
FIG. 12 illustrates that the peptide hormone insulin-like peptide 3 (INSL3) protects CLL cells from spontaneous apoptosis. The study involved the incubation of CLL cells for 72 hr with varying concentrations (1-400 nM) of the LGR8 agonist INSL3 and then assessment of "spontaneous" apoptosis of the cells by staining the cells for surface expression of Annexin V. The data are results from 4 sets of cells and show a decrease in apoptosis in response to INSL3 from about 5% to approximately 15%, thus implying that LGR8 activation can decrease apoptosis and thus, that an LGR8 antagonist would be expected to increase apoptosis of CLL cells.

This example demonstrates that CLL cells express more LGR8 mRNA and protein than do normal peripheral blood mononuclear cells or normal B cells (see FIGS. 10 & 11). The LGR8 agonist INSL3 protects CLL cells from programmed cell death (apoptosis) (see FIG. 12).

In summary, the invention provides GPCR arrays, identified patterns, uniquely expressed GPCRs in patient samples including differences in indolent vs. aggressive and testing available drugs for their ability to alter $2^{nd}$ messengers (e.g., cAMP) and to kill CLL cells. Antibody generation from orphan GPCRs is also provided and used for the same purpose.

The invention provides both diagnostic and therapeutic applications. For diagnostic purposes, for example, the invention provides biomarkers, including but not limited to, the GPCRs listed in the above Tables 1-9 for CLL disease severity, progression, prediction of clinical course and drug selection. For therapeutic purposes, for example, the invention provide new strategies to promote killing of CLL cells when used alone and in combination with currently used agents plus others in development.

REFERENCES

1. Insel P A, Zhang L, Murray F, Yokouchi H, Zambon A C. Cyclic AMP is both a pro-apoptotic and antiapoptotic second messenger. *Acta Physiolog* (Oxford) 2012; 204: 277-87.
2. Insel P A, Snead A, Murray F, Zhang L, Yokouchi H, Katakia T, Kwon O, Oimucci O, Wilderman A. GPCR expression in tissues and cells: are the optimal receptors being used as drug targets? *Brit. J Pharmacol* 2012; 165: 1613-6.
3. Peiró A M, Tang C M, Murray F, Zhang L, Brown L M, Chou O, Rassenti L, Kipps T A, Insel P A. Genetic variation in phosphodiesterase (POE) 7B in chronic lymphocytic leukemia: overview of genetic variants of cyclic nucleotide PDEs in human disease. *J Hum Genet.* 2011 September; 56(9):676-81.
4. Malavasi F, Oeaglio S, Damle R, Cutrona G, Ferrarini M, Chiorazzi N. C038 and chronic lymphocytic leukemia. a decade later. *Blood.* 2011; 118: 3470-8.
5. Zent C S, Kay N E. Management of patients with chronic lymphocytic leukemia with a high risk of adverse outcome: the Mayo Clinic approach. *Leuk Lymphoma* 2011; 52: 1425-34.
6. Zhang L, Murray F, Rassenti L Z, Pu M, Kelly C, Kanter J R, Greaves A, Messer K, Kipps T J, Insel P A. Cyclic nucleotide phosphodiesterase 7B mRNA: an unfavorable characteristic in chronic lymphocytic leukemia. *Int J Cancer.* 2011 Sep. 1; 129(5):1162-9.
7. Ben-Ami I, Yao Z, Naor Z, Seger R. Gq protein-induced apoptosis is mediated by AKT kinase inhibition that leads to protein kinase C-induced c-Jun N-terminal kinase activation. *J Biol Chem.* 2011; 286: 31022-31.
8. Macor P, Secco E, Zorzet S, Tripodo C, Celeghini C, Tedesco F. An update on the xenograft and mouse models suitable for investigating new therapeutic compounds for the treatment of B-cell malignancies. *Curr Pharm Des.* 2008; 14:2023-39.
9. Zhang L, Murray F, Zahno A, Kanter J R, Chou D, Suda R, Fenlon M, Rassenti L, Cottam H, Kipps T J, Insel P A. Cyclic nucleotide phosphodiesterase profiling reveals increased expression of phosphodiesterase 78 in chronic lymphocytic leukemia. *Proc Nat Acad Sci USA.* 2008; 105: 19532-7.
10. Yanamadala V, Negoro H, Gunaratnam L. Kong T, Denker B M. Ga12 stimulates apoptosis in epithelial cells through JNK1-mediated Bcl-2 degradation and up-regulation of IKBa. *J Biol Chem.* 2007; 282: 24352-63.
11. Burger J A, Kipps T J. CXCR4: a key receptor in the crosstalk between tumor cells and their microenvironment. *Blood.* 2006; 107: 1761-7.
12. Burger J A, Tsukada N, Burger M, Zvaifler N J, Dell'Aquila M, Kipps T J. Blood-derived nurse-like cells protect chronic lymphocytic leukemia B cells from spontaneous apoptosis through stromal cell derived factor-1. *Blood.* 2000; 96:2655-63.

The invention claimed is:

1. A method for inducing apoptosis in chronic lymphocytic leukemia (CLL) cells or inhibiting CLL cell proliferation comprising administering to a subject in need a composition comprising an effective amount of an agent that induces apoptosis in CLL cells or inhibits CLL cell proliferation and targets one or more G-protein coupled receptors (GPCR) uniquely expressed in CLL cells, wherein said GPCR is VIPR1, and wherein said agent is vasoactive intestinal polypeptide (VIP) that increases apoptosis in CLL cells.

2. The method of claim 1, wherein said composition further comprises a cyclic AMP phosphodiesterase 4/7 inhibitor selected from the group consisting of (4-(3-chloro-4-methoxyphenyl)-2-(1-mor-pholine-4-carbonyl)piperadin-4-yl)-4a,5,8,8a-tetrahydrophthalazin-1(2H)-one (IR284) and adrenocorticotropic hormone (ACTH).

* * * * *